United States Patent [19]
Pan et al.

[11] Patent Number: 5,912,007
[45] Date of Patent: Jun. 15, 1999

[54] DELIVERY SYSTEM FOR THE LOCALIZED ADMINISTRATION OF MEDICAMENTS TO THE UPPER RESPIRATORY TRACT AND METHODS FOR PREPARING AND USING SAME

[75] Inventors: Pauline C. Pan, Morris Plains; Shan Shan Sheu, Randolph; Shiuh J. Luo, Livingston, all of N.J.

[73] Assignee: Warner-Lambert Company, Morris Plains, N.J.

[21] Appl. No.: 08/761,458

[22] Filed: Dec. 6, 1996

Related U.S. Application Data

[60] Provisional application No. 60/012,539, Feb. 29, 1996.
[51] Int. Cl.$^6$ .............................. A61K 47/36; A61K 9/20
[52] U.S. Cl. .......................... 424/440; 424/439; 424/441
[58] Field of Search .................................... 514/948, 817; 424/439, 440, 441

[56] References Cited

U.S. PATENT DOCUMENTS

| | | | |
|---|---|---|---|
| 4,139,627 | 2/1979 | Lane et al. ............................... | 514/948 |
| 4,572,832 | 2/1986 | Kigasawa et al. ........................ | 424/19 |
| 4,695,463 | 9/1987 | Yang et al. .............................. | 424/440 |
| 4,702,916 | 10/1987 | Geria ...................................... | 514/817 |
| 4,843,098 | 6/1989 | Shaw et al. .............................. | 514/778 |
| 4,857,331 | 8/1989 | Shaw et al. .............................. | 424/440 |
| 4,981,698 | 1/1991 | Cherukuri et al. ......................... | 426/5 |
| 5,004,595 | 4/1991 | Cherukuri et al. ........................ | 424/48 |
| 5,147,648 | 9/1992 | Bannert .................................. | 424/535 |
| 5,314,915 | 5/1994 | Rencher .................................. | 514/535 |
| 5,330,761 | 7/1994 | Baichwal ................................ | 424/469 |

FOREIGN PATENT DOCUMENTS

| | | |
|---|---|---|
| 221850 | 5/1987 | European Pat. Off. . |
| 9203124 | 3/1992 | WIPO . |

*Primary Examiner*—Peter F. Kulkosky
*Attorney, Agent, or Firm*—Linda A. Vag

[57] ABSTRACT

The present invention pertains to delivery systems for the localized administration of a medicament to the upper respiratory tract. The delivery system comprises:

(a) a safe and effective amount of a medicament useful for treating the upper respiratory tract, (b) an ionic polysaccharide, and, (c) a cross-linking agent.

This invention also pertains to the medicated compositions containing the targeted delivery system in a pharmaceutically acceptable carrier. The invention further pertains to methods for preparing and using the delivery systems and medicated compositions.

27 Claims, No Drawings

DELIVERY SYSTEM FOR THE LOCALIZED ADMINISTRATION OF MEDICAMENTS TO THE UPPER RESPIRATORY TRACT AND METHODS FOR PREPARING AND USING SAME

This application claims priority to provisional application Ser. No.: 60/012,539 filed: Feb. 29, 1996.

BACKGROUND OF THE INVENTION

1. Field of the Invention

The present invention pertains to delivery systems for the localized administration of a medicament to the upper respiratory tract and medicated compositions containing the delivery systems. The system comprises (a) a safe and effective amount of a medicament useful for treating the upper respiratory tract; (b) an ionic polysaccharide; and, (c) a cross-linking agent. This invention also relates to methods for preparing and using the delivery systems and compositions.

2. Description of the Background

Pharyngitis, the acute inflammation of the pharnyx, is characterized, inter alia, by sore throat and painful swallowing. Painful swallowing is also often associated with laryngitis, the inflammation of the larynx. Patients suffering from sore throat and painful swallowing seek medication which can provide rapid onset of relief as well as sustained local action. Present therapeutic lozenge formulations do not provide sustained local therapeutic effects because of salivary dilution and rapid swallowing. Moreover, anesthetic-type lozenges tend to have a numbing effect on the entire mouth and tongue area and are not targeted to the oral pharyngeal area.

Various materials and techniques have been used to trap active ingredients and control their release. U.S. Pat. No. 4,695,463 discloses a particulate delivery system comprising an insolubilized active ingredient selected from the group consisting of flavoring agents, drugs, coloring agents, sweetening agents, perfumes, and bulking agents, entrapped in a cross-linked alginate or carrageenate matrix.

U.S. Pat. No. 5,330,761 discloses a controlled release, solid tablet comprising a bioadhesive mixture of a heterodisperse gum matrix and a bioadhesive agent selected from the group consisting of carbomer, polycarbophil and polyethylene oxide combined with an inert diluent and an active ingredient.

U.S. Pat. No. 5,147,648 discloses the improved adherence of gels to the mucous membranes by the separate application to the same area two components capable of forming a gel such as a metallic salt and a polysaccharide. One of the two components is used as a carrier for medicaments.

U.S. Pat. No. 4,843,098 discloses an ingestible substantially anhydrous aggregate comprising a pre-swelled hydrocolloid which partially entraps and binds a drug substrate. The hydrocolloid is selected from the group consisting of carboxymethyl cellulose, methyl cellulose, karaya gum, acacia gum, sodium alginate, calcium alginate, and hydroxypropyl methyl cellulose. The substrate is selected from the group consisting of potassium chloride, calcium carbonate, magnesium oxide, cholestyramine, and N-acetyl procainamide.

U.S. Pat. No. 4,857,331 discloses a sugarless ingestible gel confectionery delivery system comprising by weight of the final delivery system (a) a pectin gel component in an amount from about 1% to about 5%, (b) an algin gel component in an amount from about 0.2% to about 1.5%, (c) a polymer network gel component in an amount of up to about 5%, and (d) an edible insoluble solid in an amount sufficient to strengthen the internal gel network such that the gel retains its structural integrity during mold removal.

U.S. Pat. No. 4,981,698 discloses a sweetener delivery system comprising (a) a first solid natural or artificial high intensity sweetener; (b) a first inner coating selected from hydrophobic and hydrophobic coating materials, wherein the inner coating and first sweetener are mixed and prepared to form a core; and (c) a second outer coating of a hydrophobic polymer containing a second sweetener. The second outer coating is selected from the group consisting of gum arabic, tragacanth, karaya, ghatti, agar, alginates, carrageenans, furcellaran, and psyllium.

U.S. Pat. No. 5,004,595 discloses a free-flowing particulate delivery system comprising (a) a core comprising a flavor in particulate form; and (b) an encapsulating matrix for the core, wherein the matrix comprises an outer coating of a hydrophobic polymer containing an intense sweetener. The outer coating is selected from the group consisting of gum arabic, tragacanth, karaya, ghatti, agar, alginates, carrageenans, furcellaran, and psyllium.

While the above compositions provide various means for controlling the release of ingredients, none of the above compositions are entirely satisfactory for the targeted localized administration of a medicament to the upper respiratory tract.

SUMMARY OF THE INVENTION

The present invention pertains to delivery systems for the localized administration of a medicament to the upper respiratory tract. The delivery system comprises:

(a) a safe and effective amount of a medicament useful for treating the upper respiratory tract, (b) an ionic polysaccharide, and, (c) a cross-linking agent.

This invention also pertains to the medicated compositions containing the targeted delivery system in a pharmaceutically acceptable carrier. This invention further pertains to methods for preparing and using the delivery systems and medicated compositions.

DETAILED DESCRIPTION OF THE INVENTION

As used herein, the term "upper respiratory tract" refers to the larynx, throat and oral pharyngeal area. The present invention provides for the controlled, in situ formation of a thin, bioadhesive film which may bind to the buccal epithelial cells which form the surface of said upper respiratory tract. Said film formation occurs when the delivery system of the present invention comprising a medicament, an ionic polysaccharide and a cross-linking agent, in a pharmaceutically acceptable carrier, is slowly ingested by dissolution through salivation of the pharmaceutically acceptable carrier. By a series of cross-linking reactions, the cross-linking agent polymerizes the ionic polysaccharide to a film in the form of aggregates, which bind to the buccal epithelial cells in the upper respiratory tract. During the in situ cross-linking reaction, the medicament becomes entrapped in the bioadhesive polymer aggregate and thereafter is gradually released, i.e., becomes available through dissolution. The timing of the cross-linking reaction can be controlled through selection of (a) the ionic polysaccharide, (b) the cross-linking agent, and further, through selection of (c) the pharmaceutically acceptable carrier.

Because the film binds to buccal epithelial cells, the novel delivery system provides both targeted and sustained effects to the upper respiratory tract. Because the delivery systems are targeted delivery systems, compositions containing anesthetic-type agents will minimally affect the mouth and the tongue.

The delivery system may be employed to administer a wide variety of medicaments to the upper respiratory tract. The term "medicament" as used herein refers to drugs and pharmaceuticals useful for treating the upper respiratory tract and may be selected from a wide variety of water-soluble and water-insoluble medicaments. Nonlimiting illustrative categories of such medicaments include analgesics, topical anesthetics, antitussives, topical antimicrobials, antihistamines, decongestants, expectorants, cell and tissue healing agents, bronchodilators, steroidal anti-inflammatory agents, and mixtures thereof.

Nonlimiting illustrative specific examples of topical anesthetic agents include dyclonine, promazine, phenol, hexyl resorcinol, lidocaine, benzocaine, benzyl alcohol, butacaine and their pharmaceutically acceptable salts.

Nonlimiting illustrative specific examples of analgesic agents include acetylsalicylic acid, salicylic acid, acetaminophen, ibuprofen, phenacetin, phenylbutazone, salicylamide, meclofenamic acid, naproxen, sulindac, diflunisal, piroxicam, indomethacin, etodolac, fenoproben, ketoprofen, mefenamic acid, nabumetone, ketorolac tromethamine, diclofenac, evening primrose oil (containing about 72% linoleic acid and about 9% gamma-linolenic acid), mesalamine, salsalate, diflunisal, salicylsalicylic acid, choline magnesium trisalicylate and their pharmaceutically acceptable salts.

Nonlimiting illustrative specific examples of antitussive agents include menthol, camphor, dextromethorphan, dextromethorphan, noscapine, carbetapentane, chlophedianol, codeine, carmiphen and diphenhydramine, hydrocodone, hydromorphone, forminoben, noscapine and their pharmaceutically acceptable salts.

Nonlimiting illustrative specific examples of topical antimicrobial agents include cetylpyridinium chloride, quaternary ammonium salts, chlorhexidine, essential oils such as thymol, menthol and eucalyptol, methyl salicylate, hexetidine, triclosan, stannous fluoride, sanguinarine, zinc salts, sodium lauryl sulfate and the like.

Nonlimiting illustrative specific examples of antihistamine agents include chlorpheniramine, brompheniramine, phenindamine, pyrilamine, methapyrilene, doxylamine, pheniramine, diphenhydramine, dexbrompheniramine, azatadine, cyproheptadine, hydroxyzine, clemastine, bromdiphenhydramine, chlorcyclizine, thonzylamine, prilamine, dexchlorpheniramine, triprolidine, acrivastine, astemizole, azelastine, cetirizine, ebastine, ketotifen, lodoxamide, loratidine, levocabastine, mequitazine, oxatomide, setastine, tazifylline, temelastine, terfenadine and their pharmaceutically acceptable salts.

Nonlimiting illustrative specific examples of decongestant agents include phenylephrine, phenylpropanolamine, pseudoephedrine, ephedrine, propylhexedrine, xylometazoline, naphazoline, oxymetazoline and their pharmaceutically acceptable salts.

Nonlimiting illustrative specific examples of expectorant agents include guaifenesin, glyceryl guaiacolate, N-acetyl cysteine, terpin hydrate, bromhexine, ambroxol, ammonium chloride and their pharmaceutically acceptable salts.

Nonlimiting illustrative specific examples of cell and tissue healing agents include natural products such as aloe, primrose oil, fatty acids, Vitamin E, herbal extracts, botanicals and the like.

Nonlimiting illustrative specific examples of steroidal anti-inflammatory agents include flunisolide, triamcinoline, triamcinoline acetonide, beclomethasone diproprionate, betamethasone diproprionate, hydrocortisone, cortisone, dexamethasone, prednisone, methyl prednisolone, and prednisolone and their pharmaceutically acceptable salts.

Nonlimiting illustrative specific examples of bronchodilator agents include ephedrine, epinephrine, racepinephrine, terbutalin, atropine, aminophylline, isoprenaline, metaproterenol, bitoterol, theophylline and their pharmaceutically acceptable salts.

The delivery system may be used to deliver other medicaments. Nonlimiting illustrative categories of such medicaments include antiasmatic agents, antibacterial agents, antifungal agents, antinauseant agents, antipyretic agents, antiviral agents, immunostimulating agents, nutritional supplements, and various alkaloid agents such as caffeine and codeine.

Preferably, the medicament is selected from the group consisting of anesthetics, analgesics and antitussives. More preferably the medicament is dyclonine, menthol, phenol, hexyl resorcinol or benzocaine.

The medicament of the present invention may be used in many distinct physical forms well known in the pharmaceutical art to provide an initial dosage of the medicament and/or a further time-release form of the medicament. Without being limited thereto, such physical forms include free forms and encapsulated forms, and mixtures thereof.

As used herein the term "safe and effective amount" means an amount of a medicament high enough when administered orally to significantly positively modify the condition to be treated, but low enough to avoid serious side effects. The amount of medicament used in the present invention may vary depending upon the recommended or permitted therapeutic dosage for the particular active agent. Such dosages are known to the skilled practitioner in the medical arts and are not a part of the present invention. In general, the amount of medicament in the medicated composition of the present invention may vary from 0.001% to 12% by weight of the total medicated composition.

The ionic polysaccharides of the present invention are bioadhesive agents which have the ability to entrap a medicament useful for treating the upper respiratory tract. As used herein the term "ionic polysaccharide" refers to polysaccharides comprised of saccharide monomers having an acidic nature, e.g., saccharide monomers having —COOH or —SO$_4$H groups. Ionic polysaccharides belong to a group of substances generally known as hydrocolloids. These substances are strongly hydrophilic macromolecular materials that dissolve or disperse in water, producing a thickening or viscosity effect. Hydrocolloids are both natural and synthetic materials. Natural hydrocolloids are derived from both plant and animal sources. Ionic polysaccharides which may be used in the practice of the present invention may be selected from natural hydrocolloids. Preferred for use in the present invention are algin, carrageenan and pectin with the use of algin especially preferred. Algin and pectin have several carboxylic acid groups along their polymer chains while carrageenan contains sulfuric acid groups. It is preferred to use a monocationic salt of the acid, especially the sodium salt, for solubility considerations, i.e., the salt being more soluble in the aqueous environment of the oral cavity. These ionic polysaccharides swell when hydrated and change from a water-soluble solid to a gel in the presence of multivalent cations such as calcium or magnesium. The multivalent cation forms stable bridges between neighboring molecules resulting in the gel formation. If a suitable amount of the multivalent cation is used precipitation of the film can occur. Where the monovalent cationic salt is used this can occur during a chemical exchange of a multivalent ion for a monovalent ion.

Algin is a generic designation of the derivatives of alginic acid. Alginic acid is a mixed polymer of β-(1–4)-ID-mannosyluronic acid and I-(1–4)-L-gulosyluronic acid, the relative proportions of which vary with the botanical source and state of maturation of the giant kelp plant *Macrocystis pyrifera* from which algin is derived. The magnitude and kinetics of the cross-linking reaction of the algin can be controlled by varying the L-guluronic acid and D-mannurinic acid content (also known as G and M blocks). G blocks, having a more buckled, ribbon-like structure will gel quicker. Alginic acid higher in D blocks will be more delayed.

Carrageenan is extracted from Irish moss *Chondrus crispus*. It consists of alternating copolymers of J-(1–3)-D-galactose and (1–4)-3,6-anhydro-D- or L-galactose. Family members differ in the amount of sulfate ester and/or other substituent groups they carry. They are identified as R-, S- and Q-carrageenan. Kappa and iota form gels, kappa forming stronger gels than iota. Kappa-carrageenan contains only one sulfate group in each disaccharide repeating unit. Iota-carrageenan is the most highly sulfated member of the family.

Pectin is a generic name for a range of products derived from the cell walls of plant tissue classified as pectinic acids. Pectin substances are polymers of 1–4 linked I-galacturonic acid that exist in varying degrees of esterification or neutralization. They are coiled molecules rather than straight. The best gel formation is obtained with pectins wherein the methoxyl level has been reduced.

The amount of ionic polysaccharide in the delivery systems of the present invention may vary depending upon the type of polysaccharide and the type of medicament in the delivery system, as well as the particular result desired. The desirable amount of ionic polysaccharide present will also depend on the pharmaceutical carrier. The ionic polysaccharide may be added to the formulation in a proportion of from 10:1 to 1:10 by weight to the medicament although a ratio of 5:1 to 1:5 by weight would be preferred. It is not a requirement of the present invention that all of the medicament be trapped by the bioadhesive film. Wherein an upper amount of 12% medicament is present in the medicated composition and 1% ionic polysaccharide it is possible that not all of the medicament may be trapped by the film. In general, the ionic polysaccharide will be from about 0.001% to about 1.0%, more preferably from about 0.01% to about 0.6%, by weight of the total medicated composition. For pharmaceutical carriers such as a cooked candy mass wherein processing adversely affects ionic polysaecharides, a lower amount of polysaccharide is desirable.

The cross-linking agents of the present invention are cationic salts that react with the ionic polysaccharide to form a cross-linked polymeric film which adheres to the upper respiratory tract. The rate of gel formation as well as the quality and texture of the resultant gel can be controlled by the solubility and availability of the cation source. Nonlmiting illustrative categories of such cross-linking agents are the salts of multivalent cations such as aluminum, calcium, copper, iron, magnesium, manganese, zinc, and the like, and mixtures thereof. Nonlimiting examples of useful cross-linking compounds are the chloride, sulfate, acetate, and carboxylate salts of calcium, magnesium, copper, zinc, manganese, aluminum, iron, and the like. The preferred multivalent cations are bivalent, and the preferred bivalent cation is calcium. Preferably, the cross-linking agent may be selected from the group consisting of calcium carbonate, stearate, lactate, tartrate, sulfate, chloride, monocalcium phosphate, tricalcium phosphate, dicalcium phosphate dihydrate and mixtures thereof. More preferably, the cross-linking agent is calcium lactate.

The amount of cross-linking agent in the delivery systems of the present invention may depend upon the type of ionic polysaccharide employed as well as the particular result desired, more specifically, the degree of film formation to be achieved. The cross-linking agent may be added to the formulation in amounts sufficient to substantially polymerize the ionic polysaccharide present. Preferably for monocationic salts an excess of multivalent cations are added to insure substantial replacement of the monovalent cation with the multivalent cation.

In general, the amount of cross-linking agent in the delivery system will be from about 0.001% to about 1.2%, more preferably from about 0.01% to about 0.8%, by weight of the total medicated composition.

In another embodiment, the cross-linking agent is premixed with a sequestering agent to further control the timing of the cross-linking reaction. Sequestering agents are compounds that prevent ions from exhibiting their usual properties because of close combination with the sequestering agent. In the present invention, a sequestering agent can form a coordination complex with the metallic ions of the cross-linking agent to delay precipitation of the bioadhesive agent. Nonlimiting examples of useful sequestering agents may be selected from the group consisting of sodium citrate, tetrasodium phosphate, sodium hexametaphosphate, ethylene diamine tetraacetic acid and the like.

It is preferred to use a sequestering agent in a non-solid application such as in a medicated liquid center wherein the sequestering agent delays an otherwise too rapid polymerization of the ionic polysaccharide. The amount of sequestering agent in the delivery system of the present invention may vary depending upon the cross-linking agent employed and the particular result desired. In general, the amount of sequestering agent in the delivery system will be from about 0.001% to about 1.2%, more preferably from about 0.01% to about 0.8% by weight of the total medicated composition.

Although the sequestering agent may be used per se in the delivery system, it is preferred to use a pharmaceutically acceptable acid in conjunction with the sequestering agent. The pharmaceutically acceptable acids of the present invention are slow-dissolving compounds that react with the sequestered cross-linking agents to release the agent so that the later can react with the monovalent cation salts to form a polymeric film. The timing of the cross-linking reaction can be controlled through selection of the appropriate slow-dissolving pharmaceutically acceptable acid. Nonlimiting examples of useful pharmaceutically acceptable acid are citric, fumaric, malic. tartaric, lactic, adipic, phosphoric, benzoic, glutamic, sorbic, propionic, erythorbic, tannic, succinic, aconitic, and ascorbic. Preferably, the pharmaceutically acceptable acid is selected from the group consisting of citric, fumaric, malic, tartaric, lactic, adipic, and phosphoric. More preferably, the pharmaceutically acceptable acid is citric acid.

The amount of the pharmaceutically acceptable acid in the delivery systems of the present invention may vary depending upon the type of cross-inking agent employed as well as the particular result desired. In general, the amount of pharmaceutically acceptable acid in the delivery system will be from about 0.00% to about 1.2%, more preferably from about 0.01% to about 0.8% by weight of the total medicated composition.

In yet another embodiment, the release of a soluble medicament can be delayed by premixing the medicament with a pharmaceutically acceptable oil and an emulsifier, wherein the emulsifier has a hydrophilic-lipophilic balance in the range from about 1 to about 10. Nonlimiting examples of useful pharmaceutically acceptable oils may be selected from the group consisting of animal, vegetable, and marine oils, fats, and waxes (such as sunflower oil or shark liver oil), and synthetic oils, fats, and waxes. More preferably, the pharmaceutically acceptable oils are selected from the group consisting of vegetable oils and the like. Most preferably, the pharmaceutically acceptable oil is a vegetable oil. In general, the amount of pharmaceutically acceptable oil in the delivery system will be from about 0.001% to about 1%, more preferably from about 0.01% to about 0.2%, by weight of the total medicated composition.

Nonlimiting examples of useful emulsifiers having a hydrophilic-lipophilic balance in the range from about 1 to about 10 may be selected from the group consisting of decaglycerol decaoleate, lecithin and sorbitan fatty acid esters. Preferably, the emulsifier is decaglycerol decaoleate. In general, the amount of emulsifier in the delivery system will be from about 0.001% to about 1%, more preferably from about 0.01% to about 0.6% by weight of the total medicated composition.

The present invention also concerns medicated compositions comprising the targeted delivery systems. These medicated compositions comprise
(a) a safe and effective amount of a medicament useful for treating the upper respiratory tract,
(b) an ionic polysaccharide,
(c) a cross-linking agent, and,
(d) a pharmaceutically acceptable carrier suitable for administering of a medicament to the upper respiratory tract.

By "pharmaceutically acceptable carrier" is meant one or more filler or encapsulating or carrier materials which are suitable for oral administration to a human. Pharmaceutically acceptable carrier materials suitable for the preparation of dosage forms for oral administration are well-known in the art. The delivery systems useful for the localized administration of a medicament to the upper respiratory tract may be utilized in a wide variety of pharmaceutically acceptable carriers. Various oral dosage forms can be used including but not limited to such solid forms as lozenges, tablets, capsules, granules, and bulk powders and liquid centers such as syrups and suspensions.

The pharmaceutically acceptable carrier of the present invention may contain conventional excipients and additives which function to facilitate processing or storage. Thus coloring agents, flavoring agents, perfumes, sweetening agents, surface active agents, lubricants, softeners, glidants, stabilizing agents, and the like, and mixtures thereof, may be present in the medicated composition. The pharmaceutically acceptable carrier material including optional additives is present in a quantity sufficient to bring the total amount of the medicated composition to 100%.

The present invention is also directed to methods for preparing the medicated compositions. In a specific embodiment, the present invention is directed at a method for preparing a medicated composition useful for the localized administration of medicaments to the upper respiratory tract which comprises the steps of:
(1) providing the following ingredients:
(a) a medicament useful for treating the upper respiratory tract;
(b) an ionic polysaccharide;
(c) a cross-liking agent; and,
(d) a pharmaceutically acceptable carrier suitable for administering of a medicament to the upper respiratory tract;
(2) admixing the ingredients from step (1) to form the composition.

The present invention is also directed to a method for treating the upper respiratory tract. In a specific embodiment the present invention is directed at the local administration of a medicament to the upper respiratory tract which method comprises orally administering to a patient a medicated composition which comprises:
(a) a safe and effective amount of a medicament useful for treating the upper respiratory tract,
(b) an ionic polysaccharide,
(c) a cross-linking agent, and,
(d) a pharmaceutically acceptable carrier suitable for administration of a medicament to the upper respiratory tract.

An important aspect of the present invention includes a hard or soft confectionery composition incorporating the inventive delivery systems and a method for preparing the hard or soft confections. In this form of the invention, the medicated compositions includes the delivery system and a pharmaceutically acceptable carrier such as a confectionery bulking agent, and various additives. The confectionery may be in the form of a lozenge, tablet, toffee, nougat, suspension, chewy candy, and the like. The pharmaceutically acceptable carriers may be prepared from a wide range of materials. Without being limited thereto, such materials include diluents, binders and adhesives, lubricants, disintegrants, coloring agents, bulking agents, flavoring agents, sweetening agents and miscellaneous materials such as buffers and adsorbents in order to prepare a particular medicated confection.

The preparation of confectionery formulations is historically well known and has changed little through the years. Confectionery items have been classified as either "hard" confectionery or "soft" confectionery. The medicated compositions of the present invention can be incorporated into confectionery compositions by admixing the inventive compositions into conventional hard and soft confections.

As used herein, the term confectionery material means a product containing a bulking agent selected from a wide variety of materials such as sugar, corn syrup, and the like, and in the case of sugarless bulking agents, sugar alcohols such as sorbitol and mannitol and the like, and mixtures thereof. Confectionery material may include such exemplary substances as lozenges, tablets, toffee, nougat, suspensions, chewy candy, chewing gum and the like. The buking agent is present in a quantity sufficient to bring the total amount of confectionery composition to 100%.

Lozenges are flavored medicated dosage forms intended to be sucked and held in the mouth. Lozenges may be in the form of various shapes such as flat, circular, octagonal and biconvex forms. The lozenge bases are generally in two forms: hard, boiled candy lozenges and compressed tablet lozenges.

Hard boiled candy lozenges may be processed and formulated by conventional means. In general, a hard boiled candy lozenge has a base composed of a mixture of sugar and other carbohydrate bulking agents kept in an amorphous or glassy condition. This amorphous or glassy form is considered a solid syrup of sugars generally having from about 0.5% to about 3% moisture. Such materials normally contain up to about 92% sugar, up to about 55% corn syrup and from about 0.1% to about 5% water, by weight of the final composition. The syrup component is generally prepared from corn syrups, but may include other materials. Further ingredients such as flavoring agents, sweetening agents, acidulants, coloring agents and the like may also be added.

Boiled candy lozenges may also be prepared from nonfermentable sugars such as Isorbitol, mannitol, isomalt, and hydrogenated starch hydrolysates. Typical hydrogenated starch hydrolysates are LYCASIN®, a commercially available product manufactured by Roquette Corporation, and HYSTAR®, a commercially available product manufactured by Lonza, Inc. The candy lozenges may contain up to about 95% sorbitol, a mixture of sorbitol and mannitol in a ratio from about 9.5:0.5 up to about 7.5:2.5, and hydrogenated starch hydrolysates to about 55%, by weight of the solid syrup component.

Boiled candy lozenges may be routinely prepared by conventional methods such as those involving fire cookers, vacuum cookers, and scraped-surface cookers also referred to as high speed atmospheric cookers.

Fire cookers involve the traditional method of making a boiled candy lozenge base. In this method, the desired quantity of carbohydrate bulking agent is dissolved in water by heating the agent in a kettle until the bulking agent dissolves. Additional bulking agent may then be added and the cooking continued until a final temperature of. 145° C. to 156° C. is achieved. The batch is then cooled and worked as a plastic-like mass to incorporate additives such as flavoring agents, coloring agents and the like.

A high-speed atmospheric cooker uses a heat-exchanger surface which involves spreading a film of candy on a heat exchange surface, the candy is heated to 165° C. to 170° C. in a few seconds. The candy is then rapidly cooled to 100° C. to 120° C. and worked as a plastic-like mass enabling incorporation of the additives, such as flavor agents, coloring agents and the like.

In vacuum cookers, the carbohydrate bulking agent is boiled at a temperature from about 125° C. to about 132° C., vacuum is applied and additional water is boiled off without extra heating. When cooking is complete, the mass is a semi-solid and has a plastic-like consistency. At this point, flavoring agents, coloring agents, and other additives are admixed in the mass by routine mechanical mixing operations.

The optimum mixing required to uniformly mix the flavoring agents, coloring agents and other additives during conventional manufacturing of boiled candy lozenges is determined by the time needed to obtain a uniform distribution of the materials. Normally, mixing times of from about 4 to about 10 minutes have been found to be acceptable.

Once the boiled candy lozenge has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, Pharmaceutical Dosage Forms, Volume 1: Tablets (1989), Marcel Dekker, Inc., New York, N.Y. at Medicated Confections, pages 419–582, which disclosure is incorporated herein by reference.

In contrast, compressed tablet confections contain particulate materials and are formed into structures under pressure. These confections generally contain sugars in amounts up to about 95%, by weight of the composition, and typical tablet excipients such as binders and lubricants as well as flavoring agents, coloring agents and the like.

In addition to hard confectionery materials, the lozenges of the present invention may be made of soft confectionery materials such as those contained in nougat. The preparation of soft confections, such as nougat, involves conventional methods, such as the combination of two primary components, namely (1) a high boiling syrup such as a corn syrup, hydrogenated starch hydrolysate or the like, and (2) a relatively light textured frappe, generally prepared from egg albumin, gelatin, vegetable proteins, such as soy derived compounds, sugarless milk derived compounds such as milk proteins, and mixtures thereof. The firappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of a bulking agent such as a sugar, corn syrup, or a hydrogenated starch hydrolysate. Conventionally, the final nougat composition is prepared by the addition of the "bob syrup" to the frappe under agitation, to form the basic nougat mixture. Further ingredients such as flavoring agents, additional carbohydrate bulking agents, coloring agents, preservatives, medicaments, mixtures thereof and the like may be added thereafter also under agitation. A general discussion of the composition and preparation of nougat confections may be found in B. W. Minifie, Chocolate, Cocoa and Confectionery: Science and Technology, 2nd edition, AVI Publishing Co., Inc., Westport, Conn. (1980), at pages 424–425, which disclosure is incorporated herein by reference.

The procedure for preparing the soft confectionery involves known procedures. In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavoring agent may be added. The mixture is further mixed for an additional period until it is ready to be removed and formed into suitable confectionery shapes.

The novel medicated compositions may also be in the form of a pharmaceutical suspension. Pharmaceutical suspensions of this invention may be prepared by conventional methods long established in the art of pharmaceutical compounding.

Medicated candy is prepared by procedures similar to those used to make soft confectionery. In a typical procedure, a boiled sugar-corn syrup blend is formed to which is added a firappe mixture. The boiled sugar-corn syrup blend may be prepared from sugar and corn syrup blended in parts by weight ratio of about 90:10 to about 10:90. The sugar-corn syrup blend is heated to temperatures above about 120° C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65° C. and about 120° C.

The delivery systems of the present invention can then be added to the homogeneous mixture as the temperature is lowered to about 65° C.–95° C. whereupon additional ingredients can then be added such as flavoring agents and coloring agents. The formulation is further cooled and formed into pieces of desired dimensions.

A general discussion of the lozenge and tablet forms of confectionery may be found in H. A. Lieberman, Pharmaceutical Dosage Forms, Volume 1: Tablets (1989), Marcel Dekker, Inc., New York, N.Y. at Medicated Confections, pages 419–582, which disclosure is incorporated herein by reference.

Throughout this application, various publications have been referenced. The disclosures in these publications are incorporated herein by reference in order to more fully describe the state of the art.

The invention being thus described, it will be obvious that the same may be varied in many ways. Such variations are not to be regarded as a departure from the spirit and scope of the invention and all such modifications are intended to be included within the scope of the following claims.

The present invention is further illustrated by the following examples which are not intended to limit the effective scope of the claims. All parts and percentages in the examples and throughout the specification and claims are by weight of the final composition unless otherwise specified.

EXAMPLES

Examples 1 and 2

Examples 1 and 2 provide a comparison of a medicated cough drop containing the delivery system with a control confectionery. Menthol was used as the active agent. Table 1 below sets out the components in the drops.

TABLE 1

Medicated Drops

| | Examples | |
|---|---|---|
| Formula % | 1[a] | 2[b] |
| sucrose | 54.39 | 54.45 |
| corn syrup | 55.40 | 44.55 |
| water | 1.00 | 1.00 |
| sodium alginate[c] | 0.103 | — |
| Candy Base Portion Total | 97.338 | 97.35 |
| calcium lactate | 0.012 | — |
| menthol | 0.230 | 0.230 |
| eucalyptus oil | 0.200 | 0.200 |
| citric acid | 0.220 | 0.220 |
| salvage | 2.000 | 2.000 |
| Portion Total | 2.662 | 2.65 |
| Total | 100 | 100 | a: delivery system
b: control
c: added as a 4% solution

For example 1 the sucrose, corn syrup (80% dry solids), water and sodium alginate were heated in a cooking pot to approximately 145° C. The menthol, eucalyptus oil, citric acid, calcium lactate (premixed 1: with water) were mixed with the salvage portion and then mixed into the mass. The candy was formed by in a drop roller press sized at 2.2 g per piece. Each piece contained approximately 5 mg menthol.

A test panel evaluated the two comparative samples for degree (intensity) of cooling effects on the nasal passages, the mouth and the throat. The results of the evaluation are set out in Table 2.

TABLE 2

Test Panel

| | Examples | |
|---|---|---|
| | 1[a] | 2[b] |
| Nasal | 4.62 | 5.0 |
| Mouth | 5.75 | 5.62 |
| Throat | 6.12 | 5.25 | a: delivery system
b: control
Scale:
On a scale of 1–9 with 1 being very little and 9 being very much The control was found to have more diffuse vapor action having greater cooling effects in the nasal passages. The inventive sample provided cooling more directly to the throat area, i.e., the inventive sample had less cooling in the nasal passages and more cooling in the throat area, the targeted area.

Examples 3–6

Examples 3–6 provide a comparison of a medicated anesthetic-type lozenge containing the delivery system (3) with a control confectionery (5), a system containing a polymer added per se (4), and a commercial product (6). The components in the prepared confectionery compositions, Examples 3–5, are set out in Table 3.

TABLE 3

Anesthetic-Type Lozenge

| | Examples | | |
|---|---|---|---|
| Formula % | 3[a] | 4[b] | 5[c] |
| Sucrose | 54.39 | 54.44 | 49.49 |
| Corn Syrup | 44.50 | 44.55 | 49.49 |
| Coloring Agent | 0.01 | 0.01 | 0.01 |
| Sodium Alginate | 0.10 | — | — |
| Residual Moisture | 1.00 | 1.00 | 1.00 |
| Candy Base Portion Total | 96.05 | 97.37 | 97.41 |
| Menthol | 0.01 | 0.01 | 0.01 |
| Flavoring Agent | 0.29 | 0.29 | 0.29 |
| Citric Acid | 0.15 | 0.15 | 0.15 |
| Salvage-portion 1 | 2.00 | 2.00 | 2.00 |
| Dyclonine Hydrochloride | 0.14 | 0.14 | 0.14 |
| Decaglycerol Decaoleate | 0.14 | — | — |
| Vegetable Oil | 0.14 | — | — |
| Salvage-portion 2 | 1.00 | — | — |
| Calcium Lactate.5H$_2$O | 0.08 | — | — |
| Carbomer | — | 0.04 | — |
| Portion Total | 3.95 | 2.63 | 2.59 |
| Total | 100.00 | 100.00 | 100.00 | a: delivery system
b: polymer
c: control

For example 3, the candy base was prepared by adding the sucrose, corn syrup (80% dry solids), coloring agent (as a 1% aqueous solution), and sodium alginate (as a 4% aqueous solution) to a cooking pot with sufficient wetting water and cooking the mixture up to a temperature of about 145° C. to 150° C. The menthol, flavoring agent and citric acid were then admixed with the salvage-portion 1 (sugar and corn syrup). The dyclonine and decaglycerol decaoleate were then mixed, the vegetable oil then admixed with this mixture, and this admixture then mixed with the salvage-portion 2. The menthol-salvage admixture, dyclonine-salvage admixture, and calcium lactate hydrate (premix 1:1 with water) were then folded into the candy. The flavored candy mass was pressed through a candy drop roller and formed into candy pieces. The candy pieces were cooled and shaken and stored in a closed container with dehydrating packets.

For examples 4 and 5, the candy base was prepared by adding the sucrose, corn syrup (80% dry solids), and coloring agent (as a 1% aqueous solution) to a cooking pot with sufficient wetting water and cooking the mixture up to a temperature of about 145° C. to 150° C. The menthol, flavoring agent, citric acid, and dyclonine, and carbomer when present, were then admixed with salvage-portion 1 and this admixture was then folded into the candy. The flavored candy mass was pressed through a candy drop roller and formed into candy pieces. The candy pieces were cooled and shaken and stored in a closed container with dehydrating packets.

A consumer taste panel evaluated the throat numbing action of the confectionery compositions set out in Table 3, and also a commercial lozenge containing 0.14% dyclonine hydrochloride, for taste and efficacy in random order and the findings were pooled and averaged. The results from the taste panel are set out below in Table 4.

TABLE 4

Consumer Study

| Examples | | | | |
|---|---|---|---|---|
| | 3$^a$ | 4$^b$ | 5$^c$ | 6$^d$ |
| Overall Liking | 6.2 | 6.0 | 5.4 | 4.9 |
| Perceived Efficacy | 5.8 | 5.5 | 5.1 | 5.5 |
| Intensity of Throat Numbing | 4.9 | 4.2 | 4.6 | 4.2 |
| Intensity of Mouth Numbing | 5.5 | 5.7 | 5.5 | 4.8 | a: delivery system
b: polymer
c: control
d: commercial product containing 0.14% dyclonine hydrochloride
Scale:
Overall Liking; on a scale of 1–9, 1 being extremely disliked and 9 being extremely liked.
Perceived Efficacy: on a scale of 1–9, 1 being ineffective and 9 being effective.
Intensity of Throat Numbing: on a scale of 1–9, 1 being very little, 5 being just right, and 9 being too much.
Intensity of Mouth Numbing: on a scale of 1–9, 1 being very little and 9 being very much.

The greatest significance of these findings is that the delivery system (3) provided strongest throat numbing and overall preference. It was especially preferred over the commercial product which was more non-localized in its effect. The test also showed that consumers believed that (3) was more efficacious.

The test further showed that merely adding a polymer (4) does not provide the same result as provided by the delivery system (3) of the present invention.

We claim:

1. A medicated composition for the localized administration of a medicament to the upper respiratory tract which comprises:
   (a) a safe and effective amount of a medicament useful for treating the upper respiratory tract,
   (b) an ionic polysaccharide,
   (c) a cross-linking agent to polymerize the ionic polysaccharide wherein said cross-linking agent contains a multivalent ion selected from the group consisting of aluminum, calcium, copper, iron, magnesium, manganlese, zinc, and mixtures thereof, said components (a) (b) and (c) being incorporated into a carrier which is a soft confectionery material or a hard confectionery material, said confectionery material prepared from a high boiling syrup, said material suitable for administration of a medicament to the upper respiratory tract,
wherein said medicament is present in an amount from about 0.001% to about 12%, by weight of the delivery system, said ionic polysaccharide is present in an amount from about 0.001% to about 1%, by weight of the composition, and, said cross-linking agent is present in an amount from about 0.001% to about 1.2%, by weight of the composition,
such that said polymerization of said ionic polysaccharide takes place in said upper respiratory tract upon the dissolution of said carrier.

2. The medicated composition according to claim 1, wherein the medicament useful for treating the upper respiratory tract is selected from the group consisting of analgesics, topical anesthetics, antitussives, topical antimicrobials, antihistamines, decongestants, expectorants, cell and tissue healing agents, bronchodilators, steroidal anti-inflammatory agents, and mixtures thereof.

3. The medicated composition according to claim 2 wherein the medicament is an analgesic, topical anesthetic or antitussive.

4. The medicated composition according to claim 3 wherein the medicament is an antitussive.

5. The medicated composition according to claim 4 wherein the medicament is menthol.

6. The medicated composition according to claim 3, wherein the medicament is a topical anesthetic agent.

7. The medicated composition according to claim 6, wherein the medicament is dyclonine hydrochloride.

8. The medicated composition according to claim 1, wherein the ionic polysaccharide selected from the group consisting of algin, carrageenan and pectin.

9. The medicated composition according to claim 8 wherein the ionic polysaccharide is a monocationic salt.

10. The medicated composition according to claim 9 wherein the salt is sodium.

11. The medicated composition according to claim 1, wherein the cross-linking agent is selected from the group consisting of calcium stearate, calcium lactate, calcium tartrate, calcium sulfate, monocalcium phosphate, tricalcium phosphate, dicalcium phosphate dihydrate and mixtures thereof.

12. The medicated composition according to claim 11, wherein the cross-linking agent is calcium lactate.

13. The medicated composition according to claim 1, wherein the cross-linking agent is premixed with a sequestering agent.

14. The medicated composition according to claim 13, wherein the sequestering agent is selected from the group consisting of sodium citrate, tetrasodium phosphate, sodium hexametaphosphate, ethylene diamine tetraacetic acid.

15. The medicated composition according to claim 1, wherein the delivery system further comprises a pharmaceutically acceptable acid selected from the group consisting of citric acid, fumaric acid, malic acid, tartaric acid, lactic acid, adipic acid, phosphoric acid, benzoic acid, glutamic acid, sorbic acid, propionic acid, erythorbic acid, tannic acid, succinic acid, aconitic acid, ascorbic acid, and mixtures thereof.

16. The medicated composition according to claim 15, wherein the pharmaceutically acceptable acid is selected from the group consisting of citric acid, fumaric acid, malic acid, tartaric acid, lactic acid, adipic acid, phosphoric acid, and mixtures thereof.

17. The medicated composition according to claim 16 wherein the pharmaceutically acceptable acid is citric acid.

18. The medicated composition according to claim 1, wherein the pharmaceutically acceptable acid is present in an amount from about 0.001% to about 1.2%, by weight of the delivery system.

19. The medicated composition according to claim 1, wherein the medicament is premixed with a pharmaceutically acceptable oil and an emulsifier having a hydrophilic-lipophilic balance in the range from about 1 to about 10.

20. The medicated composition according to claim 19, wherein the pharmaceutically acceptable oil is selected from the group consisting of animal, vegetable, marine, and synthetic oils, fats, and waxes.

21. The medicated composition according to claim 19, wherein the emulsifier having a hydrophilic-lipophilic balance in the range from about 1 to about 10 is selected from the group consisting of decaglycerol decaoleate, lecithin and sorbitan fatty acid esters.

22. The medicated composition according to claim 19, wherein the pharmaceutically acceptable oil is vegetable oil and the emulsifier is decaglycerol decaoleate.

23. A method for preparing a medicated composition useful for the localized administration of medicaments to the upper respiratory tract which comprises the steps of:

(1) providing the following ingredients:
  (a) a safe and effective amount of a medicament useful for treating the upper respiratory tract,
  (b) an ionic polysaccharide,
  (c) a cross-linking agent to polymerize the ionic polysaccharide wherein said cross-lining agent contains a multivalent ion selected from the group consisting of aluminum, calcium, copper, iron, magnesium, manganese, zinc, and mixtures thereof, and,
  (d) a carrier which is a soft confectionery material or a hard confectionery material, said confectionery material prepared from a high boiling syrup, said material suitable for administration of a medicament to the upper respiratory tract, wherein said medicament is provided in an amount from about 0.001% to about 12%, by weight of the delivery system, said ionic polysaccharide is provided in an amount from about 0.001% to about 1%, by weight of the composition, and, said cross-linking agent is provided in an amount from about 0.001% to about 1.2%, by weight of the composition, such that said polymerization of said ionic polysaccharide takes place in said upper respiratory tract upon the dissolution of said carrier, and, (2) admixing the ingredients from step (1) to form the medicated composition.

24. A method for the local administration of a medicament to the upper respiratory tract of a patient which comprises orally administering a medicated composition which comprises:

(a) a safe and effective amount of a medicament useful for treating the upper respiratory tract, (b) an ionic polysaccharide, (c) a cross-linking agent to polymerize the ionic polysaccharide wherein said cross-linking agent contains a multivalent ion selected from the group consisting of aluminum, calcium, copper, iron, magnesium, manganese, zinc, and mixtures thereof, said components (a) (b) and (c) being incorporated into a carrier which is a soft confectionery material or a hard confectionery material, said confectionery material prepared from a high boiling syrup, said material suitable for administration of a medicament to the upper respiratory tract, wherein said medicament is present in an amount from about 0.001% to about 12%, by weight of the delivery system, said ionic polysaccharide is present in an amount from about 0.001% to about 1%, by weight of the composition, said, the cross-linking agent is present in an amount from about 0.001% to about 1.2%, by weight of the composition, such that said polymerization of said ionic polysaccharide takes place in said upper respiratory tract upon the dissolution of said carrier.

25. The medicated composition according to claim 1 wherein the confectionery material is in the form of a lozenge, toffee, nougat or chewy candy.

26. The method according to claim 23 wherein the confectionery material is in the form of a lozenge, toffee, nougat or chewy candy.

27. The method according to claim 24 wherein the confectionery material is in the form of a lozenge, toffee, nougat or chewy candy.

* * * * *